United States Patent [19]

Nagata et al.

[11] Patent Number: 4,731,453

[45] Date of Patent: Mar. 15, 1988

[54] PROCESS FOR PRODUCING 1, 3-DIALKYL-2-IMIDAZOLIDINONE

[75] Inventors: Teruyuki Nagata; Nobuyuki Kajimoto; Masaru Wada; Hideki Mizuta; Akihiro Tamaki, all of Fukuoka, Japan

[73] Assignee: Mitsui Toatsu Chemicals, Inc., Tokyo, Japan

[21] Appl. No.: 846,564

[22] Filed: Mar. 31, 1986

[30] Foreign Application Priority Data

Apr. 3, 1985 [JP] Japan .................................. 60-69044
Apr. 8, 1985 [JP] Japan .................................. 60-72677
Apr. 12, 1985 [JP] Japan .................................. 60-76657
Feb. 7, 1986 [JP] Japan .................................. 60-23975

[51] Int. Cl.$^4$ .......................................... C07D 233/32
[52] U.S. Cl. .................................................. 548/317
[58] Field of Search ....................................... 548/317

[56] References Cited

PUBLICATIONS

Schweitzer, C., *J. Org. Chem.*, 15, 471 (1950).
Hussain, M., et al., *J. Het. Chem.*, 8, 507 (1971).
Butler, A., et al., *J.C.S. Perkin II*, 317 (1981).

*Primary Examiner*—Richard A. Schwartz
*Attorney, Agent, or Firm*—Jeffers, Hoffman & Niewyk

[57] ABSTRACT

An improved process of producing 1, 3-dialkyl-2-imidazolidinones directly from N, N'-dialkylethylenediamine and urea with a high yield is provided, which process comprises reacting a N, N'-dialkylethylenediamine of the formula

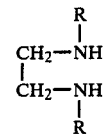

wherein R represents —CH$_3$, —C$_2$H$_5$, —C$_3$H$_7$ or —C$_4$H$_9$, with urea at 180° C. or higher in the presence of a polar solvent, to obtain a 1, 3-dialkyl-2-imidazolidinone of the formula

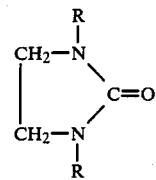

and preferably comprises carrying out the reaction at two stages, that is, the initial period reaction being carried out at 140° C. or lower to from a 1, 1'-dialkyl-1 1'-dimethylenebisurea and successively the latter reaction being carried out at 180° C. or higher.

14 Claims, No Drawings

PROCESS FOR PRODUCING 1,3-DIALKYL-2-IMIDAZOLIDINONE

BACKGROUND OF THE INVENTION

1. Field of the Invention

This invention relates to a process for producing a 1,3-dialkyl-2-imidazolidinone expressed by the formula (2)

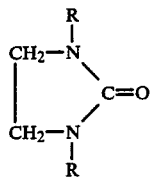
(2)

wherein R represents —CH$_3$, —C$_2$H$_5$, —C$_3$H$_7$ or —C$_4$H$_9$, by reacting a N,N'-dialkylethylenediamine expressed by the formula (1)

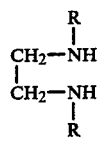
(1)

wherein R is as defined above, with urea.

1,3-Dialkyl-2-imidazolidinones expressed by the formula (2) such as 1,3-dimethyl-2-imidazolidinone are very useful substances as a polar, non-protonic solvent. In particular, they are an excellent solvent for various high molecular substances such as polyamides, polyvinyl chloride, polyvinyl alcohol, polystyrene, polyurethane, phenolic resins, etc. Further, they are a useful substance which forms a complex with many inorganic salts and dissolves, and also is used as a solvent for many organic reactions.

2. Description of the Prior Art

Among 1,3-dialkyl-2-imidazolidinones, 1,3-dimethyl-2-imidazolidinone (hereinafter abbreviated to DMI) is a generally well known compound, and as to the process for producing it, various proposals have been made.

For example, a process wherein ethylenediamine is reacted with urea to obtain 2-imidazolidinone (ethylene-urea) which is subjected to addition reaction to formalin, followed by reducing the resulting reaction product with trichloroacetic acid, formic acid or the like, into the corresponding N,N'-dimethyl compound; a process having improved the above reduction process wherein hydrogenation is carried out using a noble metal catalyst in an acidic state; a process wherein N,N'-dimethylethylenediamine is reacted with phosgene or trichloromethyl chloroformate while it is decomposed into phosgene, etc. have been known. Further, a report has been made that N,N'-dimethyleethyleneamine is reacted on heating with urea to form 1,1'-dimethyl-1,1'-dimethylenebisurea

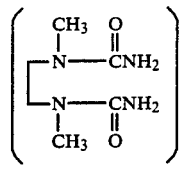

as an intermediate, which is then heated to above 300° C. to obtain DMI with a yield of 35% (Journal of the Chemical Society (Perkin Trans.) 2, (1981), 317–319).

As described, the process for producing 2-imidazolidinone by reacting ethylenediamine with urea has so far been industrially possible, but it is not easy to dialkylate the above 2-imidazolidinone into 1,3-dialkyl-2-imidazolidinone. Further, in the case of production of DMI by reacting N,N'-dimethylethylenediamine with urea, the yield is so low as described in the above literature that the process has been commercially unsatisfactory at all.

Thus if the objective compound can be produced directly from N,N'-dialkylethyleneamine and urea with a good yield, such a process is a very simple one.

SUMMARY OF THE INVENTION

A first object of the present invention is to provide a commercial production process of 1,3-dialkyl-2-imidazolidinones, particularly DMI.

A second object of the present invention is to provide an improved process of producing 1,3-dialkyl-2-imidazolidinones directly from N,N'-dialkylethylenediamine and urea with a high yield.

The present invention resides in:

In the production of a 1,3-dialkyl-2-imidazolidinone expressed by the formula (2)

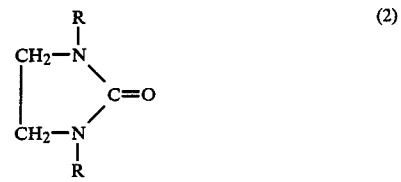
(2)

wherein R represents —CH$_3$, —C$_2$H$_5$, —C$_3$H$_7$ or —C$_4$H$_9$, by reacting a N,N'-dialkylethylenediamine expressed by the formula (1)

(1)

wherein R is as defined above, with urea, the improvement which comprises carrying out the reaction at a temperature of 180° C. or higher in the presence of a polar solvent.

According to a preferred embodiment of the present invention, the reaction is carried out at two stages provided with temperature gradient, that is, the initial period reaction forming a 1,1'-dialkyl-1,1'-dimethylenebisurea

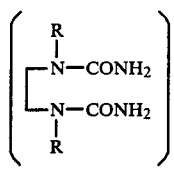

is carried out at 140° C. or lower until its formation is completed, followed by successively raising the temperature and carrying out the latter period reaction at a temperature of 180° C. or higher, and preferably 300° C. or lower. According to a more preferred embodiment of the present invention, the ratio by mol of the quantity of urea fed relative to that of the N,N'-dialkylethylenediamine at the time of the initial period reaction is made preferably 2 or less, more preferably 0.6 to 1.2 and the reaction is completed under pressure, or urea is used in a ratio by mol of about 2 at the time of the initial period reaction and N,N'-dialkylethylenediamine is additionally added at the time of heat elevation at the time of the latter stage so that the quantities of the N,N'-dialkylethylenediamine and urea used in the whole reaction may amount almost to equal mols, whereby it is possible to obtain 1,3-dialkyl-2-imidazolidinones with a higher yield according to the above reaction.

DETAILED DESCRIPTION OF THE PREFERRED EMBODIMENTS

In the present invention, as the N,N'-dialkylethylenediamine expressed by the formula (1), N,N'-dimethylethylenediamine, N,N'-diethylethylenediamine, N,N'-dipropylethylenediamine, N,N'-diisopropylethylenediamine, N,N'-dibutylethylenediamine, etc. are enumerated. When urea is reacted with these compounds, the corresponding 1,3-dialkyl-2-imidazolidinones expressed by the formula (2) are obtained. In particular, the process of the present invention is the most suitable process for commercially producing DMI from N,N'-dimethylethylenediamine.

The N,N'-dialkylethylenediamines of the formula (1) may be easily prepared from the corresponding lower monoamines according to various known methods.

For example, N,N'-dimethylethylenediamine may be obtained by reacting ethylene dichloride with an excess quantity of methylamine in water solvent.

The process of the present invention wherein these N,N'-dialkylethylenediamines and urea are used, is carried out in the presence of a polar solvent at 180° C. or higher, and in the initial period reaction of the present invention is a reaction for forming a 1,1'-dialkyl-1,1'-dimethylenebisurea as an intermediate.

Thus, in the initial period reaction, in order to inhibit the reaction of urea itself and thereby quantitatively form the 1,1'-dialkyl-1,1'-dimethylenebisurea as an intermediate, it is preferred to carry out the reaction at 180° C. or lower, preferably at 140° C. or lower.

When the initial period reaction is carried out at such a temperature or lower, reaction proceeds quantitatively between the N,N'-dialkylethylenediamine and urea, and at that time the pressure in the reactor is gradually raised by NH₃ gas released with the advance of the reaction and becomes a constant pressure before long, whereby it is possible to confirm the end point of the initial period reaction.

When the temperature is successively raised up to 180° C. or higher, preferably 200° C.–300° C., to subject the intermediate to thermal decomposition reaction, the corresponding 1,3-dialkyl-2-imidazolidinone is obtained with a high yield. If the temperature is lower than 180° C., the reaction rate is low, while if it exceeds 300° C., a problem is raised with respect of heating method.

As the solvent used in the process of the present invention, hydrocarbons and halogenated hydrocarbons are unsuitable and polar solvents are used. Examples of preferred solvents are polar, non-protonic solvents such as N,N'-dimethylformamide, N,N'-dimethylacetamide, tetramethylurea, dimethylsulfoxide, hexamethylphosphoroamide, sulfolane, methyl isobutyl ketone, nitrobenzene, tetrahydrofuran, dioxane, etc. Further, since low boiling temperatures require an excessively pressure-resistant apparatus, solvents having a boiling point of 180° C. or higher are preferred. In particular, with respect of the yield and in order to avoid the troublesome solvent separation, it is preferred to use as the solvent, the desired 1,3-dialkyl-2-imidazolidinone itself, which has been produced by the reaction.

In the process of the present invention, by using such polar solvents, it is possible to carry out a mild reaction at a relatively low temperature to obtain the desired objective product with a high yield.

The ratio of the quantity of urea fed, to that of N,N'-dialkylethylenediamine may be usually in the range of 0.5 to 2.5 in mol ratio. However, if urea of more than 2 mols relative to N,N'-dialkylethylenediamine are fed and used, i.e. if the theoretical quantity of more is used, then when the latter period higher temperature reaction is carried out at 180° C. or higher, cyanuric acid is byproduced in a large quantity to thereby reduce the yield of the objective product and result in a troublesome operation of removing it.

Thus, in order to avoid cyanuric acid formation, it is necessary to use urea in a quantity less than its theoretical equivalent, that is, less than twice by mol, preferably in the range of 0.6 to 1.2 times by mol based on N,N'-dialkylethylenediamine at the time of their feed and cause N,N'-dialkylethylenediamine to remain in the latter period reaction system, but in such a case, if unreacted N,N'-alkylethylenediamine remains in excess, it is impossible to raise the temperature up to a desired one under the atmospheric pressure since the boiling point of N,N'-alkylethylenediamine is lower than that of the latter period decomposition reaction; hence it is necessary to carry out the reaction under pressure.

In order to avoid this matter, when the initial period reaction is carried out using urea in a quantity of about 2 mols in the vicinity of equivalent based on N,N'-dialkylethylenediamine when it is fed, and successively the temperature is raised and the latter period decomposition reaction is carried out at 180° C. or higher, then if N,N'-dialkylethylenediamine is reacted while it is added, it is also possible to carry out the reaction under the atmospheric pressure. At that time, the quantity of N,N'-dimethylethylenediamine added freshly is added so that the quantity may be nearly equimolar to that of 1,1'-dimethyl1,1'-dimethylenebisurea. Namely it is preferred that the ratio of the quantities of N,N'-dimethylethylenediamine and urea used in the whole reaction be chosen so as to be nearly equimolar, and N,N'-dimethylethylenediamine be used in nearly two divided portions in the initial period reaction and the decomposition reaction step.

A concrete preferred embodiment wherein the process of the present invention is carried out under the atmospheric pressure is as follows:

Into a reactor equipped with a reflux condenser, a thermometer, a dropping funnel and a mechanical stirrer are added N,N'-dialkylethylenediamine, urea in an about equivalent quantity thereto, and as solvent a portion of the objective product itself obtained by distilling the reaction fluid under reduced pressure, each in definite quantities. The temperature is raised and reaction is carried out at 140° C. or lower. As the reaction proceeds, $NH_3$ gas is generated, and the end point of the reaction can be judged by termination of the gas generation.

The temperature is successively raised to 180° C. or higher. When the temperature reached a temperature in the vicinity of 180° C., reaction is carried out while a definite quantity of N,N'-dialkylethylenediamine is freshly dropwise added in small portions. After completion of the reaction, it is possible to take out the objective product from the reaction fluid only by direct distillation. When the objective product itself is used as the solvent for the reaction, it is unnecessary to separate it from the solvent at the time of distillation to afford a very simplified process, and after completion of the reaction, it is possible to use the distillate at the time of distillation, as it is, without purification, as the solvent for the next time reaction.

The present invention will be described in more detail by way of Examples.

EXAMPLES 1

Into a 500 ml stainless autoclave were fed N,N'-dimethylethylenediamine (88.1 g, 1.0 mol), urea (60.1 g, 1.0 mol) and DMI (100.0 g). The reaction temperature was raised up to 210° C. over about 30 minutes and reaction was carried out at the temperature for 3 hours. The pressure inside the system reached 14.5 kg/cm$^2$G as the highest pressure. After completion of the reaction, the reaction fluid was distilled and after about ⅔ of the quantity of DMI was distilled off, crystals deposited in the still residue were filtered off, followed by successively distilling the filtrate to obtain a DMI fraction (192.7 g) having a purity of 99.5% according to gas chromatography (yield: 80.8%). The still residue consisted of cyanuric acid partly containing DMI.

In addition, using various kinds of solvents in place of DMI, reaction and treatment were carried out in all the same manner as in Example 1, to obtain results shown in the following Table:

TABLE

Use of various kinds of solvents

| No. | Solvent | DMI yield (%) |
|---|---|---|
| 2 | Toluene | 5.0 |
| 3 | 1,2-Dichloroethane | 25.4 |
| 4 | Ethylene glycol | 55.5 |
| 5 | Isopropyl alcohol | 70.0 |
| 6 | Methyl isobutyl ketone | 83.0 |
| 7 | N—methyl-2-pyrrolidone | 80.5 |
| 8 | N, N'—dimethylacetamide | 82.2 |

EXAMPLE 2

Into a 500 ml stainless autoclave were fed N,N'-diethylethylenediamine (116.2 g, 1.0 mol), urea (60.1 g, 1.0 mol) and 1,3-diethyl-2-imidazolidinone (100.0 g). The temperature was raised up to a reaction temperature of 210° C. in about 30 minutes and reaction was carried out at the temperature for 3 hours.

The pressure in the system reached 14 kg/cm$^2$G as the highest pressure. After completion of the reaction, the reaction fluid was distilled, and after about ⅔ of the quantity of 1,3-diethyl-2-imidazolidinone was distilled off (boiling point: 120°–123° C./20–23 mmHg), crystals deposited in the still residue was filtered, followed by successively distilling the filtrate to obtain a fraction of 1,3-diethyl-2-imidazolidinone (214.8 g) having a purity of 99.5% according to gas chromatography (yield: 80.0%). The still residue after the distillation consisted of cyanuricacid partly containing 1,3-diethyl-2-imidazolidinone.

EXAMPLE 3

Reaction and treatment were carried out in the same manner as in Example 2 except that N,N'-diethylethylenediamine was replaced by N,N'-dipropylethylenediamine (144.3 g, 1.0 mol) and reaction was carried out in 1,3-dipropyl-2-imidazolidinone (100.0 g), to obtain 1,3-dipropyl-2-imidazolidinone having a purity of 99.7% according to gas chromatography (boiling point: 146°–148° C./20–24 mmHg, yield: 81.5%).

EXAMPLE 4

Into a 500 ml stainless autoclave were fed N,N'-dimethylethylenediamine (88.1 g, 1.0 mol), urea (60.1 g, 1.0 mol) and DMI (100 g). The temperature was raised and reaction was carried out at a reaction temperature of 120° C. for 8 hours. After start of the reaction, the pressure in the system rose gradually and became constant at 5.5 kg/cm$^2$G; thus the temperature was raised up to 210° C. in about 30 minutes, and reaction was carried out at the temperature for 3 hours. The pressure in the system reached 14.5 kg/cm$^2$G at the highest temperature. After completion of the reaction, the reaction fluid was distilled under reduced pressure to obtain a DMI fraction having a purity of 99.5% according to gas chromatography (208.6 g, yield: 94.7%). The still residue after the distillation consisted of cyanuric acid partly containing DMI.

EXAMPLE 5

Into a 500 ml stainless autoclave were fed N,N'-diethylethylenediamine (116.2 g, 1.0 mol), urea (60.1 g, 1.0 mol) and 1,3-diethyl-2-imidazolidinone (100.0 g). The temperature was raised. Reaction was carried out at a reaction temperature of 120° C. for 8 hours. After start of the reaction, the pressure in the system rose gradually and became almost constant in the vicinity of 5.5 kg/cm$^2$G; thus the temperature was successively raised up to 220° C. in about 30 minutes and reaction was carried out at the temperature for 3 hours. The pressure in the system reached 14.0 kg/cm$^2$G as the highest pressure. After completion of the reaction, the reaction fluid was distilled under reduced pressure to obtain a 1,3-diethyl-2-imidazolidinone fraction having a purity of 99.5% according to gas chromatography (237.0 g, yield: 95.5%). The still residue after the distillation consisted of cyanuric acid partly containing 1,3-diethyl-2-imidazolidinone.

EXAMPLE 6

Into a 300 ml glass flask equipped with a reflux condenser, a thermometer, a dropping funnel and a stirrer were fed N,N'-dimethylethylenediamine (44.1 g, 0.5 mol), urea (60.1 g, 1.0 mol) and DMI (100.0 g) as solvent. Into the dropping funnel was put N,N'-dimethylethylenediamine (44.1 g). The temperature was raised up to 120° C. at which reaction was carried out. As the reaction proceeds, NH₃ gas was generated and crystals separated during the reaction. After about 12 hours, NH₃ gas generation ceased. At that time, the temperature was further raised up to 210° C. Above a temperature in the vicinity of 200° C., N,N'-dimethylethylenediamine was dropwise added through the dropping funnel over about 2 hours. Reaction was then carried out at the same temperature for one hour. After completion of the reaction, the reaction fluid was distilled under reduced pressure to obtain a DMI fraction having a purity of 99.5% according to gas chromatography (211.3 g, yield: 97.0%).

What we claim is:

1. In the procedure process of 1,3-dialkyl-2-imidazolidinone expressed by the formula (2)

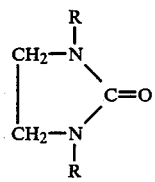
(2)

wherein R represents —CH₃, —C₂H₅, —C₃H₇ or —C₄H₉, by reacting a N,N'-dialkylethylenediamine expressed by the formula (1)

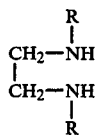
(1)

wherein R is as defined above, with urea,
the improvement which comprises carrying out the reaction at a temperature of 180° C. or higher in the presence of a non-protonic polar solvent.

2. In the production process of a 1,3-dialkyl-2-imidazolidinone expressed by the formula (2)

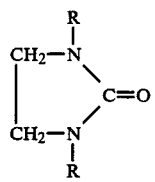
(2)

wherein R represents —CH₃, —C₂H₅, —C₃H₇ or —C₄H₉, by reacting a N,N'-dialkylethylenediamine expressed by the formula (1)

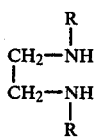
(1)

wherein R is as defined above, with urea,
the improvement which comprises reacting said N,N'-dialkylethylenediamine with urea in a quantity of twice or less by mol the quantity of said N,N'-dialkylethylenediamine in the presence of a non-protonic polar solvent at a temperature of 140° C. or lower until formation of a 1,1'-dialkyl-1,1'-dimethylenebisurea as an initial period reaction product is completed, and successively raising the temperature up to a temperature of 180° C. or higher at which the latter period reaction is then carried out under pressure.

3. In the production process of a 1,3-dialkyl-2-imidazolidinone expressed by the formula (2)

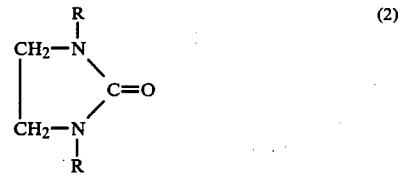

wherein R represents —CH₃, —C₂H₅, —C₃H₇ or —C₄H₉, by reacting a N,N'-dialkylethylenediamine expressed by the formula (1)

wherein R is as defined above with urea,
the improvement which comprises reacting said N,N'-dialkylethylenediamine with urea in a quantity of about twice by mol the quantity of said N,N'-dialkylethylenediamine in the presence of a non-protonic polar solvent at a temperature of 140° C. or lower until formation of a 1,1'-dialkyl-1,1'-dimethylenebisurea as an initial period reaction product is completed, and successively carrying out a latter period reaction at a temperature of 180° C. or higher while additionally adding said N,N'-dialkylethylenediamine.

4. A process according to claim 1 wherein said 1,3-dialkyl-2-imidazolidinone itself is used as said polar solvent.

5. A process according to claim 2 wherein said 1,3-dialkyl-2-imidazolidinone itself is used as said polar solvent.

6. A process according to claim 3 wherein said 1,3-dialkyl-2-imidazolidinone itself is used as said polar solvent.

7. A process according to claim 1 wherein said 1,3-dialkyl-2-imidazolidinone expressed by the formula (2) is 1,3-dimethyl-2-imidazolidinone.

8. A process according to claim 2 wherein said 1,3-dialkyl-2-imidazolidinone expressed by the formula (2) is 1,3-dimethyl-2-imidazolidinone.

9. A process according to claim 3 wherein said 1,3-dialkyl-2-imidazolidinone expressed by the formula (2) is 1,3-dimethyl-2-imidazolidinone.

10. A process according to claim 2 wherein the molar ratio of urea to said N,N'-dialkylethylenediamine is in the range of 0.6 to 1.2.

11. A process according to claim 3 wherein the quantity of said N,N'-dialkylethylenediamine additionally added in the latter period reaction at a temperature of 180° C. or higher is added so that the quantities of said N,N'-dialkylethylenediamine and urea used in the whole reaction may be nearly equimolar.

12. A process according to claim 1 wherein said reaction temperature is lower than 300° C.

13. A process according to claim 2 wherein said reaction temperature is lower than 300° C.

14. A process according to claim 3 wherein said reaction temperature is lower than 300° C.

* * * * *

UNITED STATES PATENT AND TRADEMARK OFFICE
CERTIFICATE OF CORRECTION

PATENT NO. : 4,731,453
DATED : March 15, 1988
INVENTOR(S) : Teruyuki Nagata et al It is certified that error appears in the above-identified patent and that said Letters Patent is hereby corrected as shown below:

Claim 1, Col. 7, line 15, change "procedure" to --production--.

Signed and Sealed this

Twenty-third Day of August, 1988

Attest:

DONALD J. QUIGG

Attesting Officer

Commissioner of Patents and Trademarks